United States Patent
Demmer et al.

(10) Patent No.: US 8,543,204 B2
(45) Date of Patent: Sep. 24, 2013

(54) TIMING PACING PULSES IN SINGLE CHAMBER IMPLANTABLE CARDIAC PACEMAKER SYSTEMS

(75) Inventors: Wade M. Demmer, Coon Rapids, MN (US); Paul A. Belk, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/335,249

(22) Filed: Dec. 22, 2011

(65) Prior Publication Data
US 2013/0165984 A1   Jun. 27, 2013

(51) Int. Cl.
*A61N 1/00* (2006.01)

(52) U.S. Cl.
USPC .......................................................... 607/18

(58) Field of Classification Search
USPC .......................................................... 607/18
See application file for complete search history.

(56) References Cited

U.S. PATENT DOCUMENTS

| | | | |
|---|---|---|---|
| 5,265,601 A | 11/1993 | Mehra | |
| 6,129,745 A | 10/2000 | Sun et al. | |
| 7,177,683 B2 | 2/2007 | Belk | |
| 2009/0306486 A1 * | 12/2009 | Li et al. | 600/301 |
| 2009/0306586 A1 | 12/2009 | Ross et al. | |

FOREIGN PATENT DOCUMENTS

| | | |
|---|---|---|
| EP | 0 311 019 A1 | 4/1989 |
| EP | 0 624 384 A1 | 11/1994 |

OTHER PUBLICATIONS

"Initial Clinical Experience with a Single Pass VDDR Pacing System", by Chu-Pak Lau et al., *Pacing and Clinical Electrophysiology*, November, Part II, 1992, vol. 15, pp. 1894-1900.
(PCT/US2012/068974) PCT Notification of Transmittal of the International Search Report and the Written Opinion of the International Searching Authority.

\* cited by examiner

*Primary Examiner* — George Manuel
*Assistant Examiner* — Robert N Wieland
(74) *Attorney, Agent, or Firm* — Reed A. Duthler

(57) ABSTRACT

Methods for timing pacing pulses in an implantable single chamber pacemaker create a simulated, or virtual chamber in order to apply dual chamber-type algorithms and modes. For example, a virtual atrium may be constructed based on information provided by the ventricle, that is, the timing of actual intrinsic ventricular events, and the timing of paced ventricular events, both of which may be sensed as ventricular depolarization by electrodes of the implanted system.

12 Claims, 5 Drawing Sheets

TIMING PACING PULSES IN SINGLE CHAMBER IMPLANTABLE CARDIAC PACEMAKER SYSTEMS

CROSS-REFERENCE TO RELATED APPLICATION

The present application is related to commonly-assigned and co-pending United States Patent Application, entitled METHODS FOR PROMOTING INTRINSIC ACTIVATION IN SINGLE CHAMBER IMPLANTABLE CARDIAC PACING SYSTEMS and having the Ser. No. 13/192,706, filed on Jul. 28, 2011.

FIELD OF THE DISCLOSURE

The present invention pertains to cardiac pacing and more particularly to methods for timing pacing pulses in single chamber implantable cardiac pacing systems.

BACKGROUND

The traditional implantable cardiac pacemaker includes a pulse generator device to which one or more flexible elongate lead wires are coupled. Single-chamber pacemakers generally employ at least one electrode to control the timing of pacing pulses in one chamber of the heart, either an atrium or a ventricle. Normal cardiac excitation begins in the right atrium (RA) and is transmitted to the ventricles through a specialized physiologic conduction system, so an atrial single-chamber pacemaker, which stimulates atrial depolarization, when necessary, best mimics normal physiology. However an atrial single-chamber pacemaker is only effective when the physiologic conduction system is reliable, since ventricular contraction is essential for maintaining hemodynamic perfusion. Ventricular single-chamber pacemakers provide perfusion even if the physiologic conduction system fails, but paced depolarization from a ventricular site may result in less efficient ventricular contraction and thus, inferior hemodynamic perfusion compared to normal, coordinated cardiac excitation.

Dual-chamber pacemakers generally employ atrial and ventricular electrodes, and simultaneously control the timing of pacing pulses to both the RA and one of the ventricles, either right or left. Coordinated pacing of the atrium and ventricle in such a device restores an approximation to normal cardiac contraction. In the nominal case, dual-chamber pacing coordinates atrial and ventricular depolarization, so that each atrial depolarization, whether paced or intrinsic, is followed by a ventricular depolarization, paced, if necessary. More sophisticated dual-chamber pacing algorithms also provide atrial coordination to certain ventricular events, for example inhibiting atrial pacing in response to extraneous ventricular events. However, in recent years, dual-chamber pacing algorithms have been developed to minimize ventricular pacing, for example to reduce energy consumption for increased pacemaker efficiency, while maintaining reasonable coordination between atrial and ventricular contraction.

FIG. 1A illustrates a ventricular single-chamber pacemaker 100, which includes a hermetically sealed canister 101, implanted in a subcutaneous pocket, remote from the heart, and one or more lead wires 106 extending therefrom to corresponding electrodes 111, 112 implanted in a right ventricle RV. Canister 101 may contain a pulse generator 103 like that illustrated via block diagram in FIG. 1B. With reference to FIGS. 1A-B, those skilled in the art will appreciate that pacemaker 100, via electrodes 111, 112, has the capability to sense intrinsic ventricular depolarization (i.e. R-waves) and, in the absence of the intrinsic depolarization, to apply stimulation pulses to the RV in order to create paced ventricular depolarization. Pulse generator 103 of pacemaker 100 further includes rate response sensor 135 that monitors a patient's general level of physical activity to determine an appropriate pacing rate for the patient. Examples of suitable rate response sensors include, without limitation, a force transducing sensor, such as a piezoelectric crystal like that described in commonly assigned U.S. Pat. No. 4,428,378 Anderson et al.; an AC or DC accelerometer like those described in commonly assigned U.S. Pat. No. 5,957,957 to Sheldon; and any type of physiological sensor known in the art, such as those that measure minute ventilation, QT intervals, blood pressure, blood pH, blood temperature, blood oxygen saturation etc. Numerous cardiac pacing methods that employ such RV pacing and sensing and physical activity monitoring are known in the art, for example, as disclosed in commonly assigned U.S. Pat. Nos. 4,428,378 (to Anderson et al.), 6,772,005 (to Casavant et al.), and 5,522,859 (to Stroebel et al.), as well as U.S. Pat. Nos. 5,374,281 (to Kristall et al.) and 6,122,546 (to Sholder et al.). Many of the aforementioned disclosures address the desire to limit the amount of pacing stimulation delivered from implantable pacemakers, particularly right ventricular stimulation in patients that have intact AV conduction (through the AV node, from the sinus node in the right atrial wall to the right and left bundle branches in the ventricular septum), in order to preserve the patient's natural conduction and increase pacemaker efficiency. However, the relatively more sophisticated pacing methods that are geared toward preserving the patient's natural conduction rely upon dual chamber sensing as these methods were developed in concert with the evolution of pacemaker systems from single chamber to dual chamber. Thus, there is a need for new cardiac pacing methods that preserve natural conduction and increase system efficiency for single chamber implantable pacemaker systems, like that shown in FIGS. 1A-B, or like a more compact type of pacemaker which is described in the above-referenced related U.S. patent application Ser. No. 13/192,706.

SUMMARY

Methods of the present invention apply dual-chamber pacing algorithms and modes in single-chamber pacemakers for the timing of pacing pulses, by creating a simulated, or virtual chamber. Embodiments of the present invention pertain to single chamber implantable pacemaker systems having a pulse generator that includes a microprocessor element being preprogrammed to direct the pulse generator to execute methods disclosed herein. For example, in a single chamber ventricular pacemaker, a virtual atrium is constructed based upon relationships between actual ventricular activity and simulated, or virtual atrial activity. It is also contemplated that methods of the present invention may be employed to construct a virtual ventricle that facilitates the timing of pacing pulses delivered by a right atrial single chamber pacemaker system.

BRIEF DESCRIPTION OF THE DRAWINGS

The following drawings are illustrative of particular embodiments and methods of the present invention and therefore do not limit the scope of the invention. The drawings are not to scale (unless so stated) and are intended for use in conjunction with the explanations in the following detailed description. Methods of the present invention will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1A:
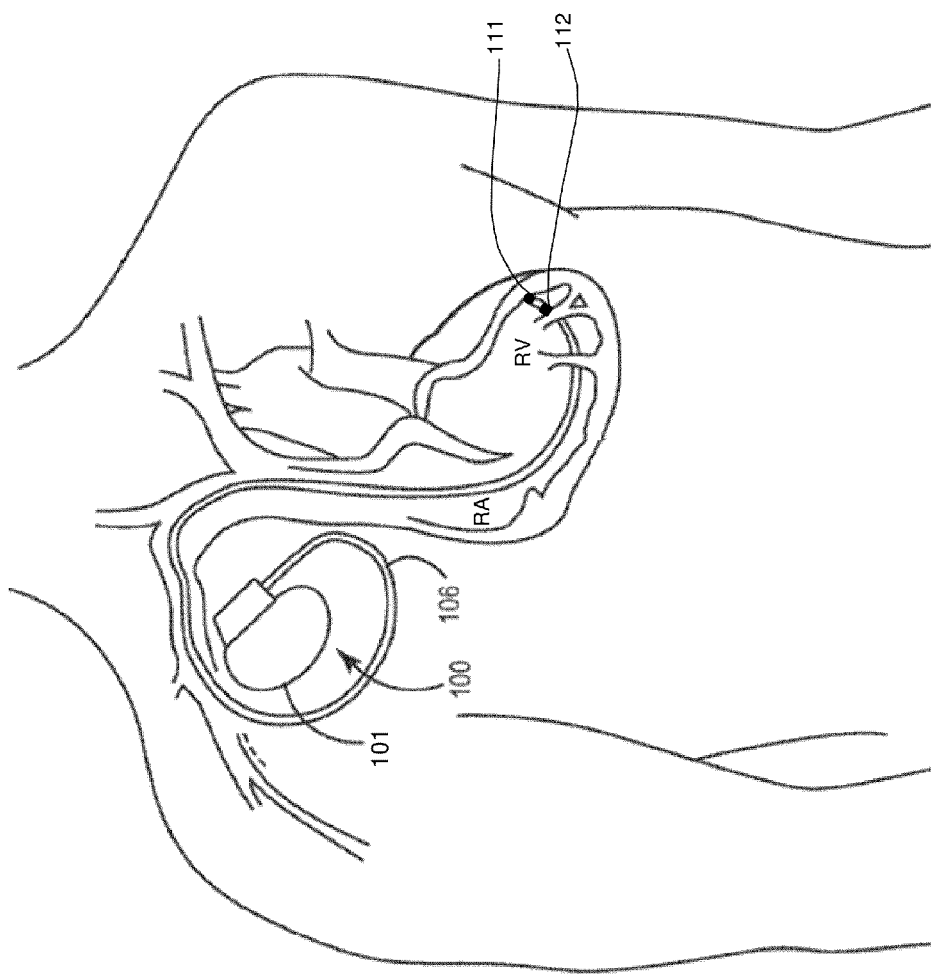
FIGS. 1A-B are schematics providing context for methods of the present invention.
Figure 1B:
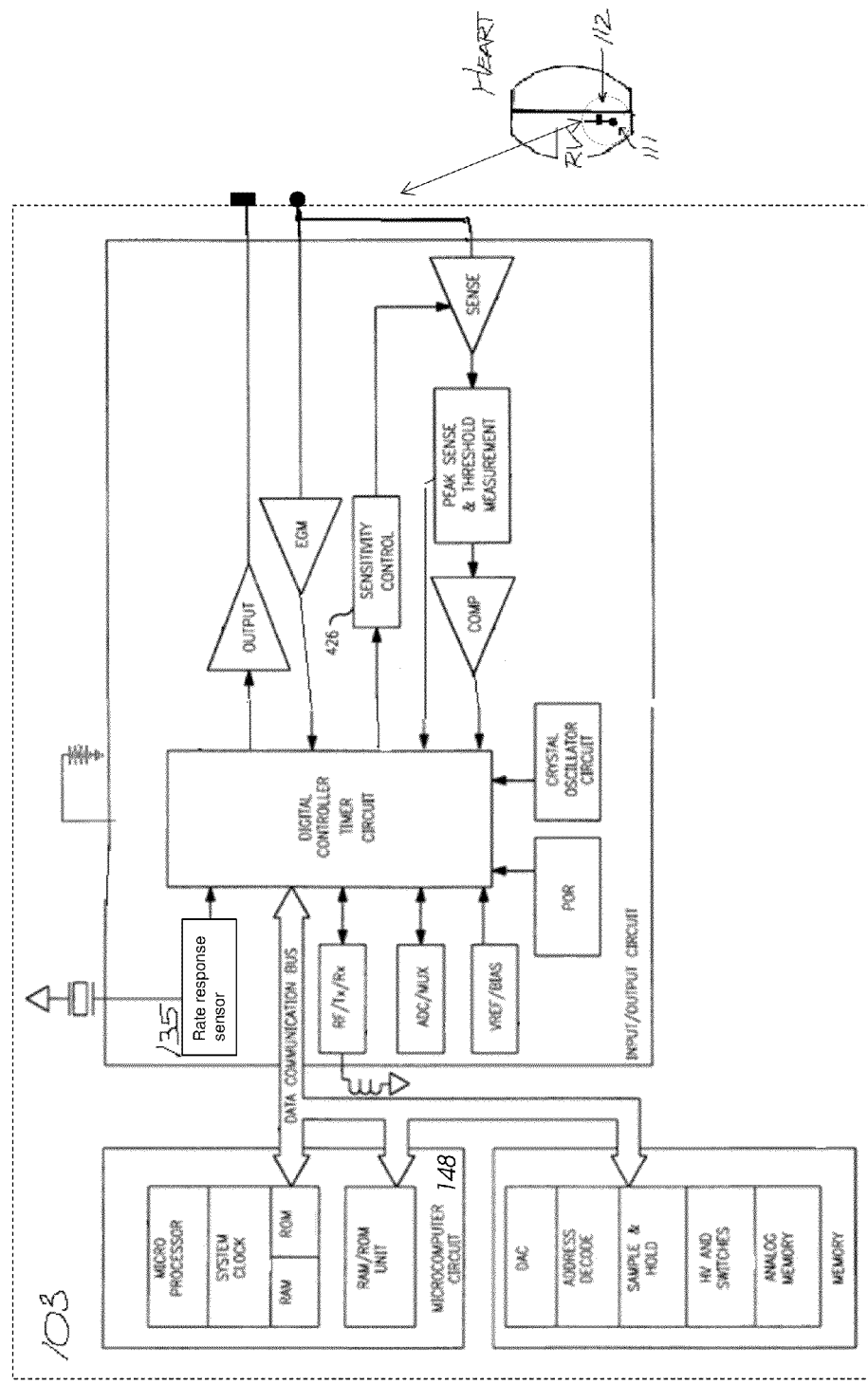
Figure 2:
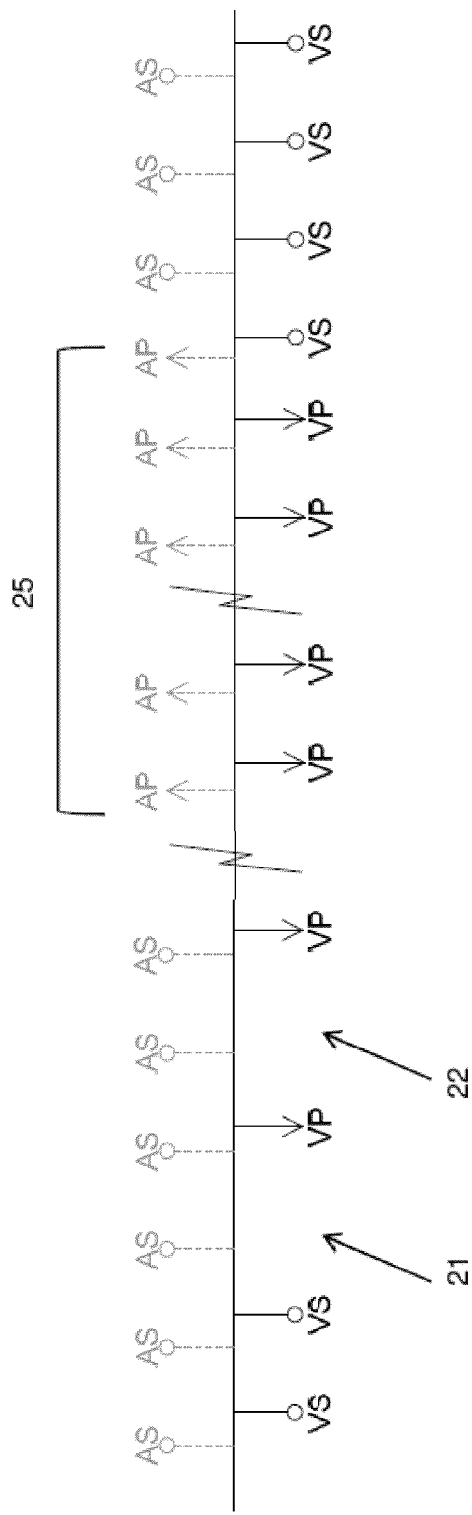
FIG. 2 is a diagram depicting a constructed virtual atrium for the application of various dual chamber pacing algorithms, according to some methods.

With reference to FIGS. 1A-B, a microcomputer circuit 148 of pulse generator 103 in single chamber ventricular pacemaker 100 is employed to construct a virtual atrium by estimating the timing of atrial depolarization, based on information provided by the ventricle, that is, the timing of actual, intrinsic ventricular events, and the timing of paced ventricular events, both of which may be sensed as ventricular depolarization by electrodes 111, 112 of the implanted pacemaker 100. FIG. 2 illustrates a simple example of the construction of a virtual atrium for the application of one or more dual-chamber pacing algorithms and modes in a ventricular single-chamber pacemaker, according to some methods of the present invention, wherein ventricular events are shown below the horizontal line, either as open circles corresponding to sensed intrinsic ventricular events, hereinafter designated VS events (i.e. sensed by electrodes 111, 112 to be detected by pulse generator 103), or as arrow tips corresponding to paced events VP, hereinafter designated VP events, which are created by the application of ventricular pacing pulses (i.e. applied by pulse generator 103 via electrodes 111, 112). Sensing in the ventricle, to collect information concerning the timing of VS events, preferably in conjunction with information provided by the above-described rate response sensor 135 of pulse generator 103, for example, gathered and processed by circuit 148, provides a good estimate of the timing of atrial activity (i.e. atrial depolarization) so that a virtual atrium may be constructed.

With reference to FIG. 2, according to some methods of the present invention, when a VS event occurs, the microprocessor element creates a simulated, or virtual atrial sensed event (open circles above the horizontal line), herein after designated AS event, that precedes the VS event by a suitable interval, which may be a fixed interval (e.g. 180 ms) or an interval determined by observations of previous ventricular behavior, hereinafter designated a virtual sensed atrial-ventricular (AV) interval, that is based on an historic rate of VS events, or, conversely, the interval between successive VS events (V-V interval), and repeatedly creates AS events synchronized with the historic V-V interval, as shown along the left hand side of the diagram in FIG. 2. According to FIG. 2, a regular pattern of atrial depolarization is assumed. When the third AS event is not followed by a VS event within the virtual sensed AV interval (i.e. a dropped beat designated with reference numeral 21), a pacing pulse is applied to create a VP event, which is timed according to the virtual sensed AV interval, following the next AS event. Absent a subsequent VS event, for example, indicated by a second dropped beat designated with reference numeral 22, another VP event is created, by the application of a pacing pulse, again following the next AS event and timed therewith according to the virtual sensed AV interval, which results in a prolonged V-V interval. The microprocessor element may continue to create AS events, according to the original virtual sensed AV interval to coordinate the application of pacing pulses following each dropped beat, according to the illustrated pattern on the left hand side of the diagram in FIG. 2, or a predetermined number of dropped beats, can trigger a mode switch, for example, illustrated on the right hand side of the diagram in FIG. 2.

FIG. 2 illustrates virtual atrial paced events (arrow tips above the horizontal line), herein after designated AP events, which are created by the microprocessor element and timed according to a virtual paced AV interval that is based on a predetermined dual chamber pacing rate. The virtual paced AV interval may be greater than virtual sensed AV interval, for example, by a predetermined increment, such as a fixed interval increment or a percentage interval increment, for example, to provide adequate support to a particular patient while minimizing any unnecessary pacing stimulation. The virtual paced AV interval may further be based on information provided by rate response sensor 135, to better track a patient's activity level. With further reference to FIG. 2, at the end of a predetermined time period 25, if a conduction check (i.e. cessation of pacing) results in the detection of a VS event (i.e. intrinsic ventricular depolarization), the microprocessor element resumes the creation of AS events to correspond with VS events at the appropriate sensed AV interval.

Figure 3:
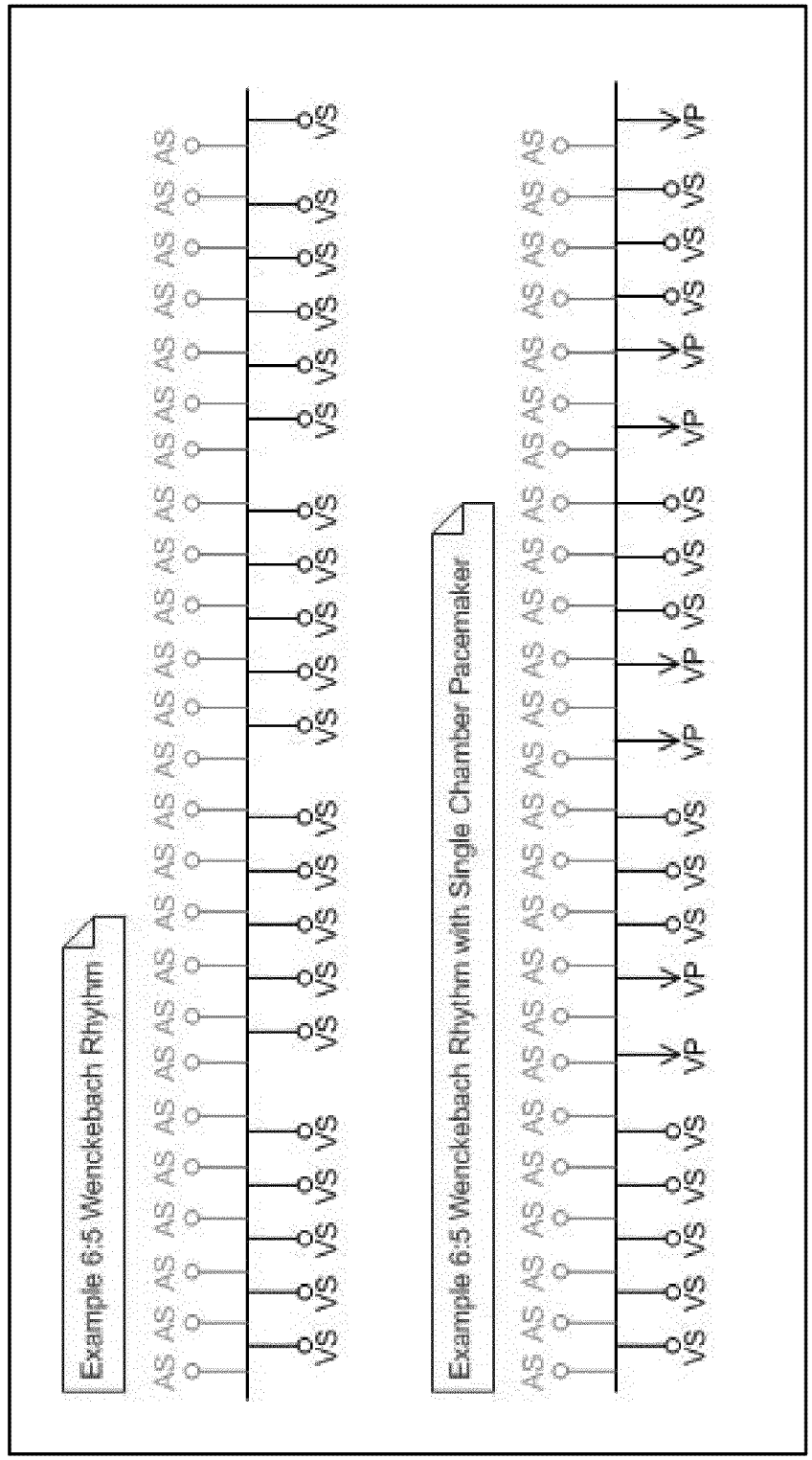
FIG. 3 is a pair of exemplary marker channel diagrams.

In other embodiments, a sequence of a number of AS events, over a more prolonged period of time, is inferred from a historic pattern of VS events over the same period, by assuming regular atrial activity and an associated consistent pattern of AV nodal activity (i.e. conduction from right atrium to ventricles). For example, two regular sequences of five VS events, each followed by a pause, may be inferred to be a 6:5 Wenckebach pattern in the AV node, in response to regular atrial activity, for example as illustrated by the exemplary marker channel diagrams shown in FIG. 3. However, in any case, each AS event is created and stored according to a virtual, or expected/suitable sensed atrial-ventricular (AV) interval, and each AP event is created and stored according to pre-determined virtual paced AV interval, which is implemented in certain circumstances.

Figure 4:
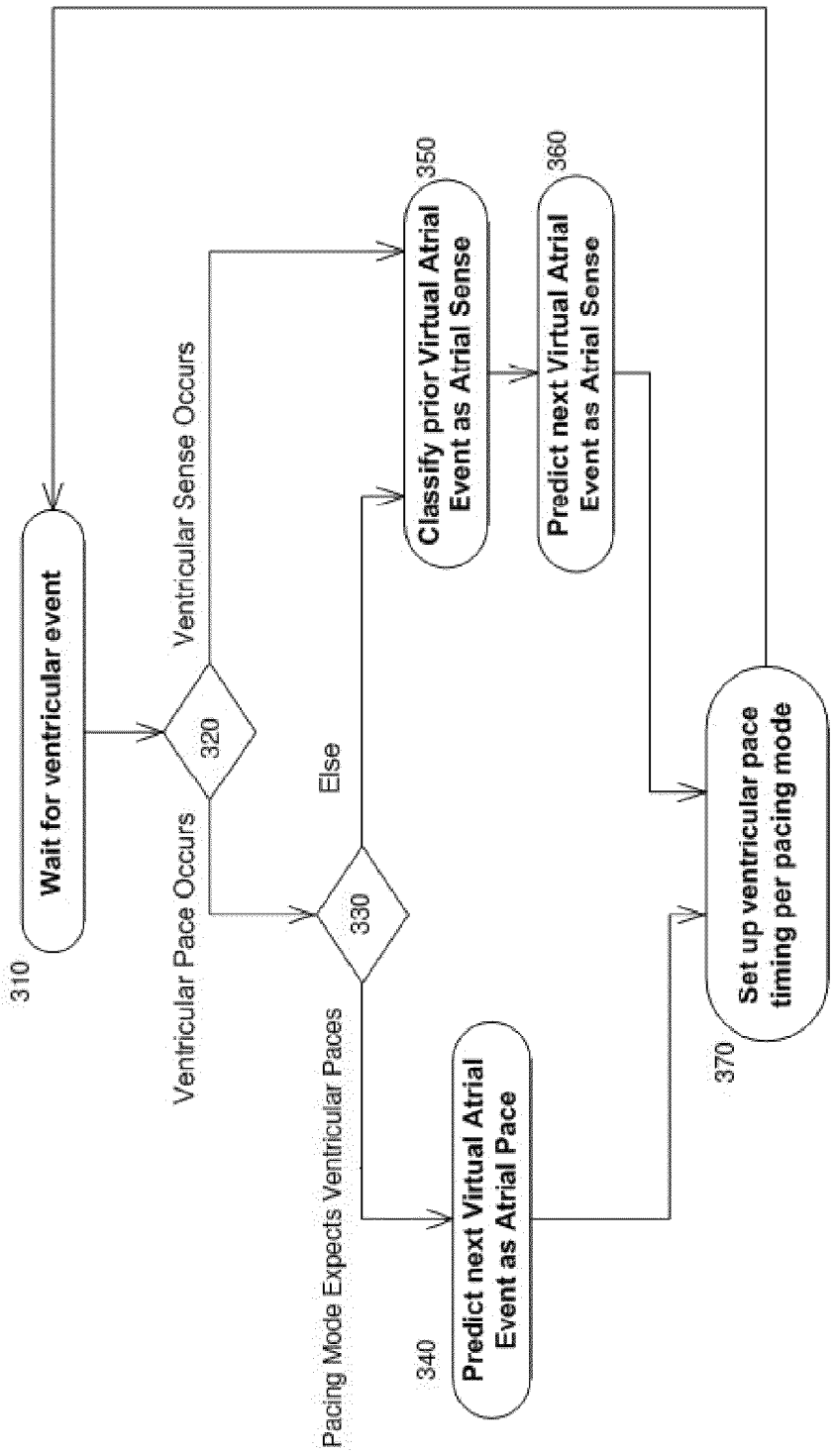
FIG. 4 is a flowchart outlining some methods of the present invention.

FIG. 4 is a flowchart outlining exemplary methods according to the above description. At step 320, which follows waiting for a ventricular event in step 310, the event is either a sensed event or a paced event (VS event or VP event, per FIG. 2). If a sensed event (320), step 350 creates and classifies a prior virtual atrial event as an atrial sense (AS event of FIG. 2), and subsequent step 360 creates a next atrial event as an AS event. Alternately, if a paced event (320), step 330 determines if the paced event is one that triggers a pacing mode switch, per step 340, in which virtual atrial paced events (AP events of FIG. 2), for example, over period of time 25 (FIG. 2), are created; otherwise step 330 leads to steps 350 and 360. In any case, dual chamber pacing algorithms may be employed to dictate the timing of ventricular pacing pulses, per step 370, as facilitated by the construction of the simulated, or virtual atrium with the above-described AS events and AP events.

The description of the invention is merely exemplary in nature and, thus, variations that do not depart from the gist of the invention are intended to be within the scope of the invention. Such variations are not to be regarded as a departure from the spirit and scope of the invention. For example, acceleration or deceleration of atrial activity could be built into the virtual atrium, as inferred from similar behavior of ventricular activity.

The invention claimed is:

1. A method for timing pacing pulses in a single chamber implantable cardiac pacemaker, the method comprising applying one or more dual chamber pacing algorithms by creating a virtual chamber.

2. The method of claim 1, wherein creating the virtual chamber comprises:
   constructing a virtual atrium by creating virtual sensed atrial events and virtual paced atrial events, the virtual sensed atrial events according to a virtual sensed AV interval, and the virtual paced atrial events according to a virtual paced AV interval, the virtual sensed and paced AV intervals being based upon intrinsic ventricular events sensed by implanted electrodes of the pacemaker; and
   applying, by means of the implanted electrodes, a ventricular pacing pulse to create a paced ventricular event that is timed according to either the virtual paced AV interval or the virtual sensed AV interval, whenever an intrinsic ventricular event is not detected by the sensing within the virtual sensed AV interval.

3. The method of claim 2, wherein the virtual sensed AV interval is further based upon a historic pattern of sensed intrinsic ventricular events.

4. The method of claim 2, wherein the virtual paced AV interval is greater than the virtual sensed AV interval.

5. The method of claim 2, wherein the virtual paced AV interval is further based upon a pre-programmed rate.

6. The method of claim 2, wherein the virtual paced AV interval is further based upon input from a rate response sensor that tracks patient activity.

7. An implantable single chamber cardiac pacemaker comprising a pulse generator having a microprocessor pre-programmed to time pacing pulses delivered by the pulse generator, according to one or more dual chamber algorithms, by creating a virtual chamber.

8. The pacemaker of claim 7, further comprising implantable electrodes coupled to the pulse generator, and wherein creating the virtual chamber comprises:
   constructing a virtual atrium by creating virtual sensed atrial events and virtual paced atrial events, the virtual sensed atrial events according to a virtual sensed AV interval, and the virtual paced atrial events according to a virtual paced AV interval, the virtual sensed and paced AV intervals being based upon intrinsic ventricular events sensed by the implantable electrodes; and
   applying, by means of the electrodes, a ventricular pacing pulse to create a paced ventricular event that is timed according to either the virtual paced AV interval or the virtual sensed AV interval, whenever an intrinsic ventricular event is not detected by the sensing within the virtual sensed AV interval.

9. The pacemaker of claim 8, wherein the virtual sensed AV interval is further based upon a historic pattern of sensed intrinsic ventricular events.

10. The pacemaker of claim 8, wherein the virtual paced AV interval is greater than the virtual sensed AV interval.

11. The pacemaker of claim 8, wherein the virtual paced AV interval is further based upon a pre-programmed rate.

12. The pacemaker of claim 8, wherein the pulse generator further comprises a rate response sensor that tracks patient activity, and the virtual paced AV interval is further based upon input from the rate response sensor.

* * * * *